(12) United States Patent
Wagner

(10) Patent No.: US 8,333,106 B2
(45) Date of Patent: *Dec. 18, 2012

(54) SYSTEM AND METHOD FOR MEASUREMENT USING A VISUAL RECORDER

(75) Inventor: Jeff A. Wagner, Long Valley, NJ (US)

(73) Assignee: Rudolph Research Analytical, Hackettstown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/052,278

(22) Filed: Mar. 21, 2011

(65) Prior Publication Data

US 2011/0167909 A1 Jul. 14, 2011

Related U.S. Application Data

(63) Continuation of application No. 12/099,453, filed on Apr. 8, 2008, now Pat. No. 7,908,903, which is a continuation-in-part of application No. 11/471,320, filed on Jun. 20, 2006, now Pat. No. 7,437,909.

(51) Int. Cl.
*G01N 9/00* (2006.01)
(52) U.S. Cl. ........................................................ 73/32 A
(58) Field of Classification Search ................. 73/32 A, 73/19.01, 19.03, 19.1
See application file for complete search history.

(56) References Cited

U.S. PATENT DOCUMENTS 4,074,562 A * 2/1978 North, Jr. ....................... 73/32 A
6,629,449 B1 * 10/2003 Kline-Schoder et al. .... 73/19.03

* cited by examiner

*Primary Examiner* — John Chapman, Jr.
(74) *Attorney, Agent, or Firm* — Kaplan Breyer Schwarz & Ottesen LLP

(57) ABSTRACT

An oscillatory measurement system is disclosed that includes a visual recorder for detecting irregularities such as bubbles in a fluid to be measured. Techniques are provided for scanning the recorder across the oscillatory tube.

7 Claims, 1 Drawing Sheet

SYSTEM AND METHOD FOR MEASUREMENT USING A VISUAL RECORDER

RELATED APPLICATION

This application is a Continuation of U.S. patent application Ser. No. 12/099,453, filed Apr. 8, 2008, entitled "Oscillatory Measurement Device With Visual Recorder", which is a Continuation-In-Part of U.S. patent application Ser. No. 11/471,320, filed on Jun. 20, 2006, which has matured into U.S. Pat. No. 7,437,909 (issued Oct. 21, 2008) entitled "Oscillatory Measurement Device With Visual Recorder", the entirety of the disclosure of which applications are hereby incorporated herein by reference.

TECHNICAL FIELD

This invention relates to density measurement, and more specifically, to an improved method and apparatus for using an oscillator to measure density or other parameters of a fluid.

BACKGROUND OF THE INVENTION

A common form of density measuring instrument is the vibrating tube type wherein a hollow oscillator is filled with a sample under test. The density is determined from a parameter of the oscillator, typically the frequency or period of oscillation.

FIG. 1 illustrates a typical such prior art arrangement. A cantilevered hollow oscillator 1 is formed of transparent material and mounted to a support 2. This support forms a node in the oscillator which defines the volume of the sample under test. Means to sustain and measure the oscillation are well known and are omitted for clarity. Rectangular area 3 represents the area viewable by the operator through a window or viewport.

Sample entrance and exit ports 4 allow introduction of the sample under test. The sample flows around the U-tube shape as shown.

The presence of small bubbles or particulates anywhere in the oscillating sample can cause errors in the density measurement. Consequently, these instruments are often constructed with clear glass oscillators and viewing windows to allow the user to visually scan the sample for bubbles or particulates during and after injection of the sample under test.

The small physical size of the bubbles makes this difficult. Furthermore the density measuring apparatus is often placed in an environment that makes viewing inconvenient, for example under a fume hood.

DETAILED DESCRIPTION OF THE PREFERRED EMBODIMENT

A video camera and display may be used to create an expanded remotable view of the oscillator. Two practical problems must be overcome to implement such a system. First, the ratio of the length of the sample filled oscillator, typically 75 mm, to the size of a small bubble of perhaps $\frac{1}{10}$ of a millimeter is very high. A magnification that would allow convenient viewing of the bubble, for example 20 times, would result in an overall image size of 1.5 meters. This size and cost of such a display is not suitable for integration into a bench-top density meter. Second, to resolve such small bubbles requires that each bubble be imaged over several pixels of the camera. Using the example figures above the resolution of the camera and display would need to be over 2000 pixels. Such cameras exist, but their cost is prohibitive. The current invention discloses a way to overcome these difficulties and provide a means of ensuring that the full length of the oscillating sample is free from small bubbles and particulates.

Figure 1:
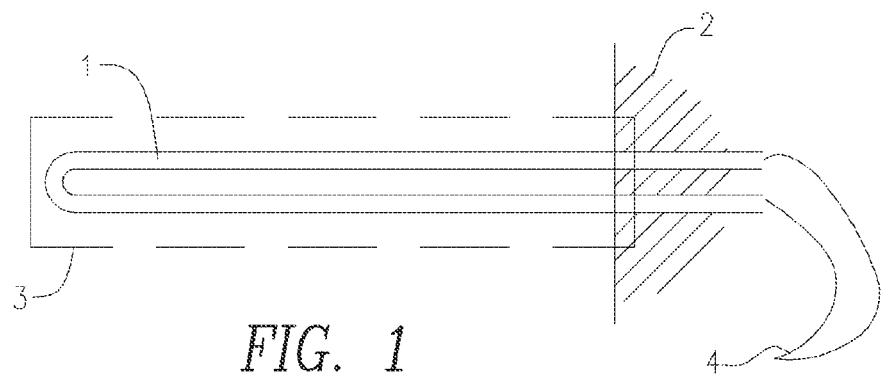
FIG. 1 is a depiction of a prior art oscillatory measurement device.
Figure 2:
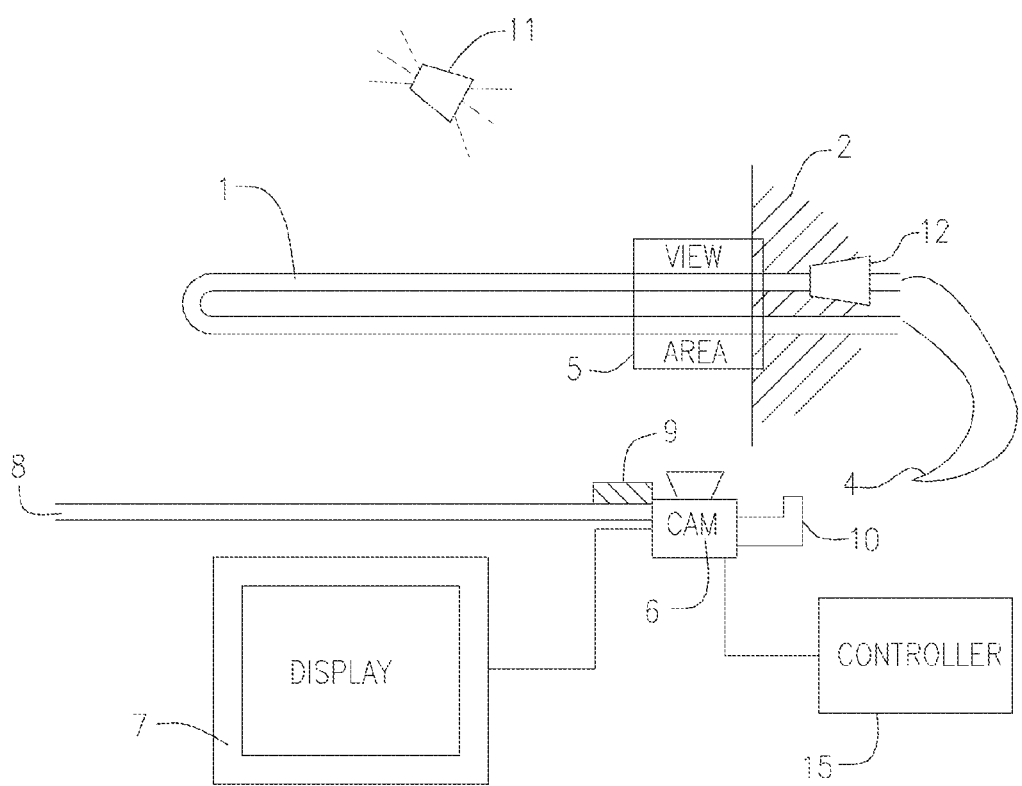
FIG. 2 depicts an exemplary embodiment of the present invention.

FIG. 2 illustrates an exemplary embodiment of the present invention. Here rectangular area 5 represents a view of a greatly reduced portion of the cantilevered hollow oscillator 1 adjacent to the node formed by support 2 including a view of the entrance and exit flows. The view of rectangular area 5 is transferred by camera and optics 6 to display 7. A controller 15 adjusts the flow rate based upon properties detected from the display.

Reducing the size of the viewed area reduces the required display size and camera resolution for a given magnification. For example a 16 mm wide viewing area imaged onto a 640 pixel wide camera would resolve a $\frac{1}{10}$ mm bubble over four pixels. At a magnification of 20 times the display would be 320 mm wide. Cameras and displays of these dimensions are economical and convenient to integrate into bench-top instrumentation.

Positioning the reduced viewed area adjacent to the node which defines the sample volume and including views of the entrance and exit flows allows the operator to scan the sample for bubbles and particulates as it is loaded. If a bubble or particulate is observed entering the oscillator, loading must continue until the bubble or particulate is observed exiting the oscillator. By this method the operator is assured that no bubbles or particulates have been introduced anywhere in the oscillator.

The detection of bubbles or particulates may be automated, such as by utilizing software that detects irregularities via image processing, and can assure that a similar irregularity exits the oscillatory tube 1 prior to measurement.

In some cases bubbles may form in the sample after loading. For instance a dissolved gas may come out of solution as a sample cools. For this case the reduced field of view may be scanned across the oscillator for example by placing the camera and optics on a linear slide 8 operated either by hand or by an actuator 9. Alternatively, the field of view of the camera 6 may be physically large enough to capture the entire oscillatory tube, but the actual field of view may be controlled and limited electronically to the field show as 5 in FIG. 2.

It is also noted that the camera may be controlled electronically so that at a particular point in the measurement process, such as when fluid begins being introduced into oscillatory tube 1, the camera begins to capture the moving image. Or, when the oscillatory tube is filled, the camera 6 automatically begins to scan the entire oscillatory tube 1. Or, both may occur as well.

Not shown in the figure, but necessary to the operation of the invention is a means of illuminating the area viewed by the camera. An illumination system that allows the operator to vary the balance between bright field illumination 11 and dark field illumination 10 is preferred. Additionally, light from a source 12 may be conducted into the viewed area by using the sample and oscillator ports as a light pipe. Light conducted along the sample is deflected by bubbles toward the camera.

The real-time simultaneous magnified view of the entrance and exit flows can provide other critical feedback to the operator as well. In some samples, microscopic bubbles are observed to adhere to the interior walls of the oscillator tube. These bubbles can resist the flushing action of the sample load and maintain their position on the oscillator wall. To detach these bubbles, the operator can momentarily increase the speed of the sample load. After the bubbles are detached, loading continues while monitoring the entrance flow for an absence of bubbles until the bubbles are observed departing with the exit flow.

Conversely, if the sample is loaded at too great a speed, the operator may observe microscopic bubbles which are formed by cavitation in the turbulent flow of the sample. In this case the operator can reduce the sample load speed until an absence of bubbles is obtained for the duration of the load.

In the examples above, the feedback from the real-time simultaneous magnified view of the entrance and exit flows allows the operator to arrive at an improved loading technique and avoid measurement errors that such microscopic bubbles caused in prior art density meters.

The above describes the preferred embodiment. The oscillator shown may be replaced with any other type of oscillator, such as that described in U.S. patent application Ser. No. 11/471,355 filed Jun. 20, 2006, entitled Method and Apparatus for Oscillating a Test Sample, That application is fully incorporated herein by reference in its entirety.

The invention claimed is:

1. A method for measuring the density of fluids comprising:
    viewing the entrance and exit fluid flows of a fluid into and out of a transparent oscillator with a camera;
    monitoring a magnified view of the entrance fluid flow; and
    continuing to load the fluid into the oscillator until every bubble, particulate or contaminant observed in the entering flow is subsequently observed in the flow exiting the oscillator.

2. The method of claim 1 further comprising altering at least one aspect of the fluid flow if monitoring step detects anything tending to introduce an error into the fluid density measurement.

3. The method of claim 1 further comprising increasing the speed of the fluid flow if bubbles are detected on an interior wall of the oscillator.

4. The method of claim 1 further comprising:
    providing a hollow oscillator having a tube for holding fluid and a visual recorder constructed to monitor only a section of said tube; and
    scanning said recorder over said tube.

5. The method of claim 4 wherein:
    said visual recorder scans electronically but not physically.

6. The method of claim 4 wherein said visual recorder scans physically but not electronically.

7. The method of claim 4 further comprising triggering said visual recorder to begin recording upon an occurrence of a predetermined event.

* * * * *